United States Patent [19]
Trozera et al.

[11] Patent Number: 5,902,475
[45] Date of Patent: May 11, 1999

[54] METHOD FOR MANUFACTURING A STENT

[75] Inventors: Thomas Trozera, Del Mar; Gary W. Gomringer, La Mesa, both of Calif.

[73] Assignee: Interventional Technologies, Inc., San Diego, Calif.

[21] Appl. No.: 08/835,015

[22] Filed: Apr. 8, 1997

[51] Int. Cl.[6] ................................................. C25F 3/00

[52] U.S. Cl. ........................ 205/655; 205/151; 205/221; 205/223; 205/229

[58] Field of Search .................................. 205/151, 209, 205/210, 212, 218, 221, 223, 224, 229, 655

[56] References Cited

U.S. PATENT DOCUMENTS

| | | | |
|---|---|---|---|
| 3,300,286 | 1/1967 | Nalband et al. | 205/151 |
| 3,644,180 | 2/1972 | Burock et al. | 205/223 |
| 4,246,328 | 1/1981 | Sato et al. | 430/5 |
| 4,547,274 | 10/1985 | Ohashi et al. | 204/129.4 |
| 4,733,655 | 3/1988 | Palmaz . | |
| 4,739,762 | 4/1988 | Palmaz . | |
| 4,776,337 | 10/1988 | Palmaz . | |
| 5,019,090 | 5/1991 | Pinchuk . | |
| 5,092,877 | 3/1992 | Pinchuk . | |
| 5,092,968 | 3/1992 | Manty | 205/221 |
| 5,098,527 | 3/1992 | Banks et al. | 205/221 |
| 5,102,417 | 4/1992 | Palmaz . | |
| 5,104,404 | 4/1992 | Wolff . | |
| 5,167,614 | 12/1992 | Tessmann . | |
| 5,183,725 | 2/1993 | Nashino et al. | 205/655 |
| 5,192,297 | 3/1993 | Hull . | |
| 5,192,307 | 3/1993 | Wall . | |
| 5,195,984 | 3/1993 | Schatz . | |
| 5,222,971 | 6/1993 | Willard . | |
| 5,226,913 | 7/1993 | Pinchuk . | |
| 5,266,073 | 11/1993 | Wall . | |
| 5,282,823 | 2/1994 | Schwartz . | |
| 5,304,200 | 4/1994 | Spaulding . | |
| 5,306,294 | 4/1994 | Winston . | |
| 5,354,308 | 10/1994 | Simon . | |
| 5,395,390 | 3/1995 | Simon . | |
| 5,397,355 | 3/1995 | Marin . | |
| 5,405,377 | 4/1995 | Cragg . | |
| 5,411,549 | 5/1995 | Peters . | |
| 5,411,551 | 5/1995 | Winston . | |
| 5,421,955 | 6/1995 | Lau . | |
| 5,423,855 | 6/1995 | Williams . | |
| 5,443,496 | 8/1995 | Schwartz . | |
| 5,449,372 | 9/1995 | Schmaltz . | |

(List continued on next page.)

FOREIGN PATENT DOCUMENTS

| | | |
|---|---|---|
| 0722700A2 | 3/1995 | European Pat. Off. . |
| 0709067A2 | 1/1996 | European Pat. Off. . |
| 0723766A1 | 7/1996 | European Pat. Off. . |

*Primary Examiner*—Kathryn Gorgos
*Assistant Examiner*—Thomas H Parsons
*Attorney, Agent, or Firm*—Michael Klicpera, Esq.

[57] ABSTRACT

Disclosed herewithin is a method of fabricating a stent which involves processing a tubular member whereby no connection points to join the edges of a flat pattern are necessary. The method includes the steps of a) removing contaminates from a tubular member, b) coating the outside surface of the tubular member with a photo-sensitive resist material, c) placing the tubular member in an apparatus designed to simultaneously rotate the tubular member while passing a specially configured photographic frame negative between a UV light source and the tubular member, thereby exposing a specified pattern of UV light to the resist coated tubular member, d) exposing the outside surface of the tubular member to a photoresist developer for a specified period of time, e) rinsing the excess developer and uncured resist from the outside surface of the tubular member, f) treating the tubular member with a electro-chemical process to remove uncovered metal. This process can lend itself to virtually an unlimited number of stent designs and configurations. By modifying the photographic frame negative, the same process can be employed to fabricate various stent designs from a tubular structure.

50 Claims, 5 Drawing Sheets

U.S. PATENT DOCUMENTS

| | | |
|---|---|---|
| 5,449,373 | 9/1995 | Pinchasik . |
| 5,464,650 | 11/1995 | Bera . |
| 5,480,519 | 1/1996 | Abbott et al. ...................... 204/129.35 |
| 5,514,154 | 5/1996 | Lam . |
| 5,569,295 | 10/1996 | Lam . |
| 5,603,721 | 2/1997 | Lau . |
| 5,616,230 | 4/1997 | Otsuka et al. ......................... 205/210 |
| 5,624,508 | 4/1997 | Flomenblit . |

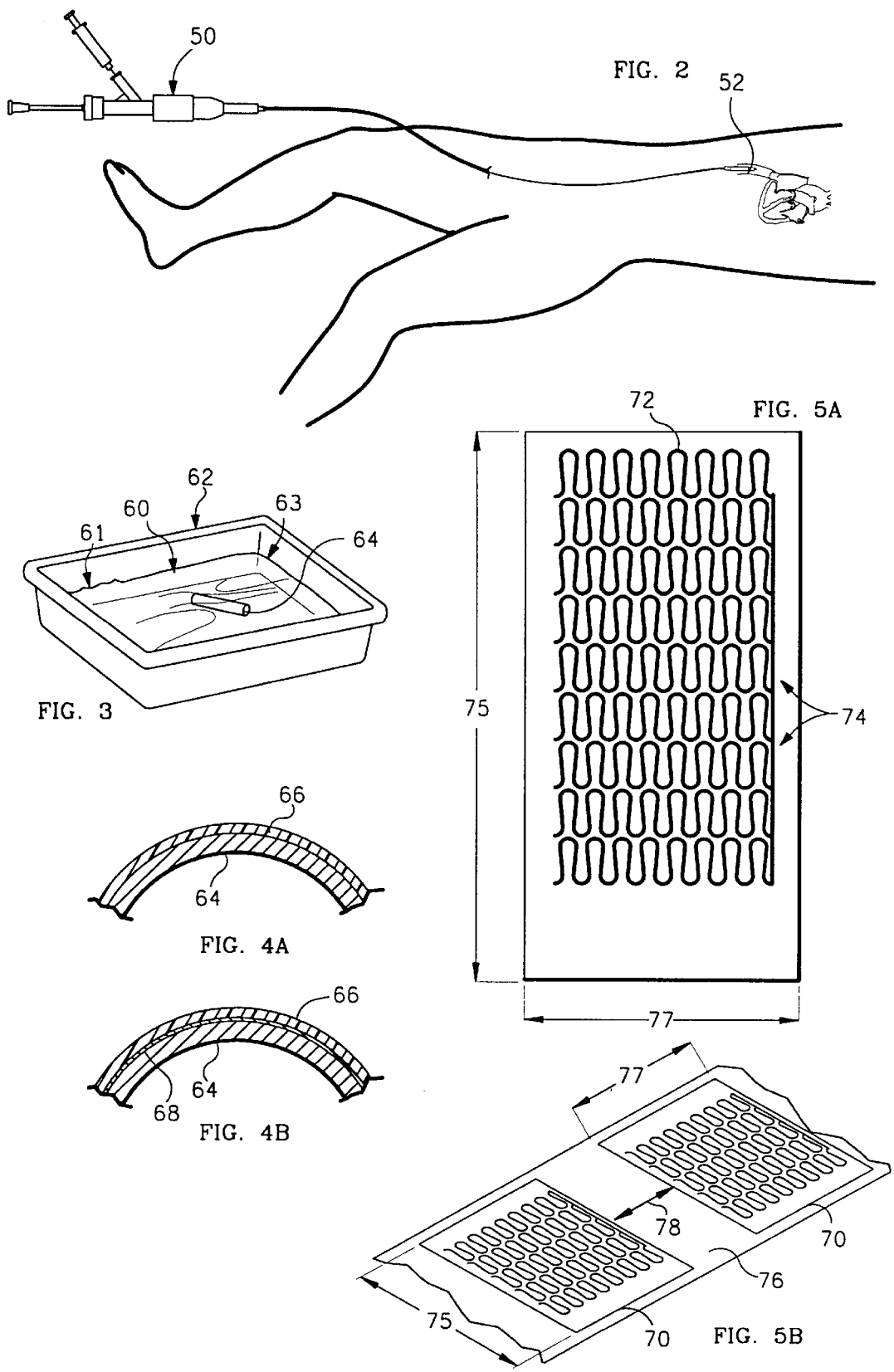

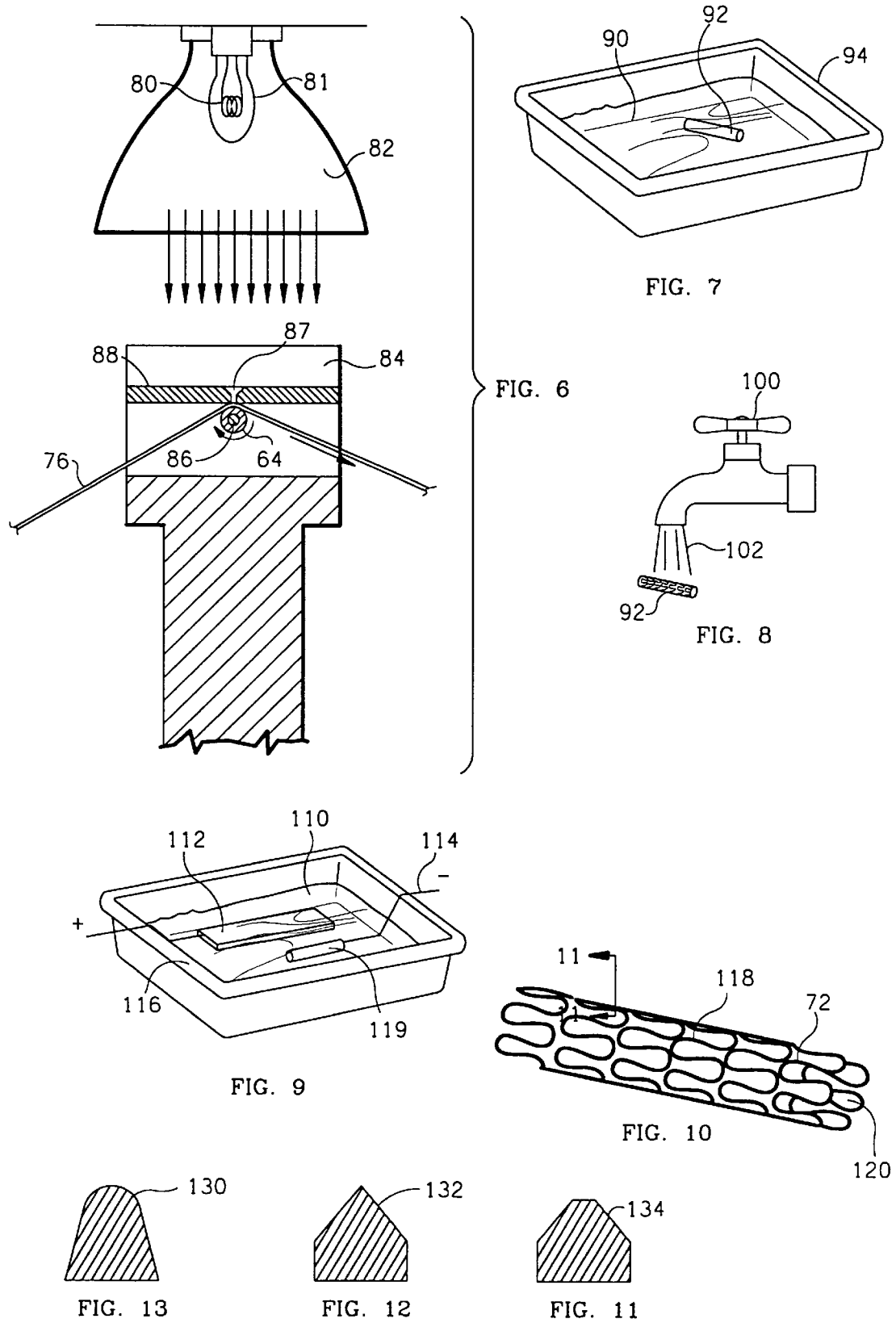

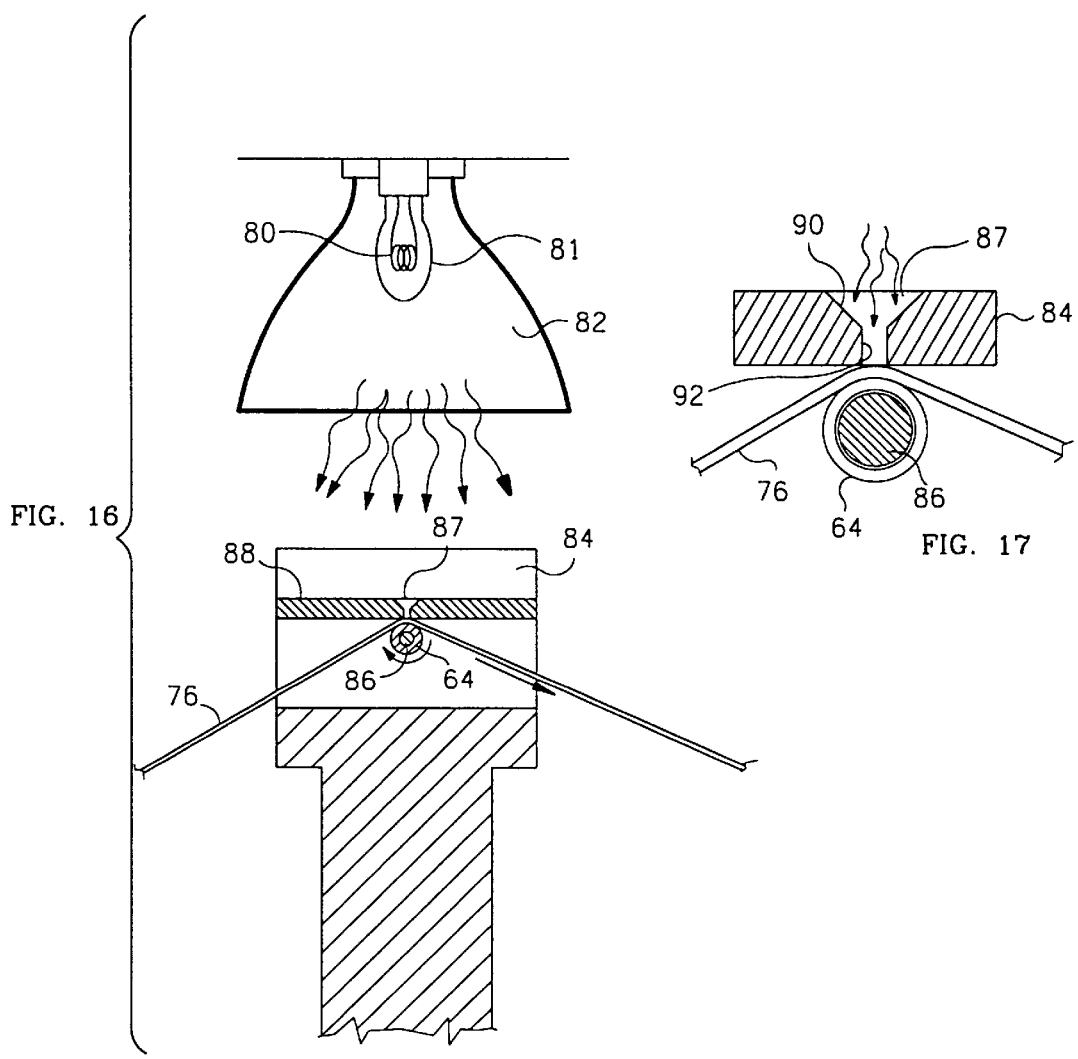
FIG. 16
FIG. 17
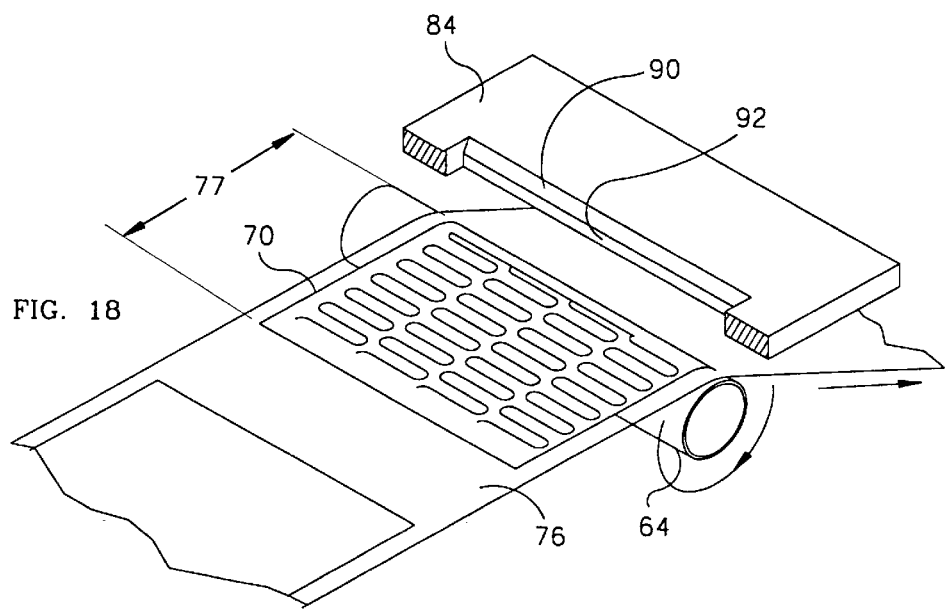
FIG. 18

METHOD FOR MANUFACTURING A STENT

FIELD OF THE INVENTION

In general, the present invention relates to percutaneous transluminal devices and methods which are used to treat obstructed (sclerotic) vessel lumina in humans. In particular, the present invention is an improved method for fabricating stents or prostheses. In addition, the improved method employs a novel apparatus.

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Conventional open heart surgery is, of course, very invasive and traumatic for patients undergoing such treatment. In many cases, less traumatic, alternative methods are available for treating cardiovascular disease percutaneously. These alternate treatment methods generally employ various types of balloons (angioplasty) or excising devices (atherectomy) to remodel or debulk diseased vessel segments. A further alternative treatment method involves percutaneous, intraluminal installation of one or more expandable, tubular stents or prostheses in sclerotic lesions. Intraluminal endovascular prosthetic grafting is an alternative to conventional vascular surgery. Intraluminal endovascular grafting involves the percutaneous insertion into a blood vessel of a tubular prosthetic graft and its delivery via a catheter to the desired location within the vascular system. The alternative approach to percutaneous revascularization is the surgical placement of vein, artery, or other by-pass segments from the aorta onto the coronary artery, requiring open heart surgery, and significant morbidity and mortality. Advantages of the percutaneous revascularization method over conventional vascular surgery include obviating the need for surgically exposing, removing, replacing, or by-passing the defective blood vessel, including heart-lung by-pass, opening the chest, and general anesthesia.

Stents or prostheses are known in the art as implants which function to maintain patency of a body lumen in humans and especially to such implants for use in blood vessels. They are typically formed of a cylindrical metal mesh which can expand when pressure is internally applied. Alternatively, they can be formed of wire wrapped into a cylindrical shape. The present invention relates to an improved method of manufacturing stents.

Stents or prostheses can be used in a variety of tubular structures in the body including, but not limited to, arteries and veins, ureters, common bile ducts, and the like. Stents are used to expand a vascular lumen or to maintain its patency after angioplasty or atherectomy procedures, overlie an aortic dissecting aneurysm, tack dissections to the vessel wall, eliminate the risk of occlusion caused by flaps resulting from the intimal tears associated with primary interventional procedure, or prevent elastic recoil of the vessel.

Stents may be utilized after atherectomy, which excises plaque, or cutting balloon angioplasty, which scores the arterial wall prior to dilatation, to maintain acute and long-term patency of the vessel.

Stents may be utilized in by-pass grafts as well, to maintain vessel patency. Stents can also be used to reinforce collapsing structures in the respiratory, biliary, urological, and other tracts.

As described in U.S. Pat. No. 4,776,337 issued to Palmaz, the cylindrical metal mesh shape is produced by laser cutting a thin walled metal tube. A laser is used to cut away all but the lines and curves of the mesh. The method of U.S. Pat. No. 4,776,337 is applicable for relatively large mesh shapes and for meshes whose lines are relatively wide. However, for more delicate and/or intricate shapes, the spot size of the laser is too large.

European Patent Application EP 0 709 067 A2 describes a stent fabrication method of preparing a flat pattern design, cutting the pattern in the flat sheet, deforming the sheet to cause the edges to touch, connecting at least the edges at least one point usually by a welding process, and then polish the finished product. The disadvantage of this process is that flat sheet must be deformed to form the final tubular configuration, and that there is a longitudinal attachment point which provides a discontinuous outer contour and a potential weak point for failure. Furthermore, the weld is metallurgically and chemically unstable and will degrade in the human body. In addition, this process requires several critical manufacturing steps which are eliminated by the present invention.

U.S. Pat. Nos. 5,514,154 and 5,421,955 describe a stent manufacturing process utilizing a computer controlled laser to selectively remove an etchant-resistant coating form a design resembling a stent. The use of a laser to selectively remove the etchant-resistant coating is a relatively expensive and complicated process. The laser must be linked to a computer controlled X–Y movement system that must precisely control the rotation and movement of the laser for stent fabrication. Variances in this process will transcend into variability in the fabricated stent. The present invention neither requires the use of an expensive laser system nor the complex movement system.

It is, therefore, an object of the present invention to provide a stent fabrication method which can produce stents with relatively intricate, delicate and detailed designs from a tubular member which negates the disadvantages of the prior designs.

In addition, it is a further object of the present invention to provide a method of fabricating a stent which involves processing a tubular member whereby no connection points to join the edges of a flat pattern are necessary.

SUMMARY OF THE INVENTION

The present invention involves a method of fabricating a stent by processing a tubular member. During the fabrication process, a novel apparatus is employed to expose a coated tubular member to a precise pattern of UV light dictated by a specifically designed film which moves over the tubular member as it is rotated.

The method of manufacture includes the steps of first electro-cleaning the tubular member with an appropriate solution. The tubular member comprises stainless steel, platinum, titanium, tantalum, gold alloy, or a gold/platinum alloy, but any number of metallic elements or polymeric materials can be employed.

Once the tubular member is cleansed of contaminates, the outer surface is uniformly coated with a photo-sensitive resist. Optionally, a coupling agent may be used to facilitate the bonding of the photo-sensitive resist to the tubular member. The coupling agent is not essential in that some tubular member compositions bond directly to the photo-sensitive resist solution without the need for a coupling agent.

This coated tubular member is then placed in an apparatus designed to rotate the tubular member while the coated tubular member is exposed to designated pattern, of ultraviolet (UV) light. The apparatus controls the exposure of the coated tubular member by utilizing a photographic film with a specified computer generated imprinted configuration, transferring the UV light in the specified pattern to the coated tubular member. The UV light activates the photosensitive resist causing the areas where UV light is present to expose (cross-link) the photo-sensitive resist. The photosensitive resist forms cross links where is it exposed to the UV light thus forming a pattern of hardened and cured polymer which mimics the particular stent design surrounded by uncured polymer. The film is adaptable to virtually an unlimited number of intricate stent designs. The process from the apparatus results in the tubular member having a discrete pattern of exposed photo-sensitive material with the remaining areas having unexposed photo-sensitive resist.

The exposed tubular member is immersed in a negative resist developer for a specified period of time. The developer removes the relatively soft, uncured photo-sensitive resist polymer and leaves behind the cured photo-sensitive resist which mimics the stent pattern. Thereafter, excess developer is removed from the tubular member by rinsing with an appropriate solvent. At this time, the entire tubular member is incubated for a specified period of time, allowing the remaining photo-sensitive resist polymer to fully cure (harden) and attach to the surface of the processed tubular member. The tubular member can be incubated at room temperature or can be exposed to a heat source in the range of 100 to 400 degrees Celsius.

The processed tubular member is then exposed to a electro-chemical etching process which removes uncovered metal from the tubular member, resulting in final tubular member or stent configuration.

This process can lend itself to virtually an unlimited number of stent designs and configurations. By modifying the film and employing the identical process one can fabricate a variety of stent designs.

The present invention will be understood and appreciate more fully from the following detailed description taken in conjunction with the drawings.

BRIEF DESCRIPTION OF THE DRAWINGS

FIG. 2 is a schematic view of the finished stent of the present invention in its intended operational environment;

FIG. 3 is a schematic representation of the first cleaning step of the manufacturing process of the present invention;

FIGS. 4(A) and (B) are cross-sectional views of the tubular member of the present invention with the optional coupling agent engaged to the outside surface of the tubular member;

FIG. 5A is a top view illustration of one frame of film with a stent configuration imprinted on the film;

FIG. 5B is a slanted top view illustration of several frames on a sheet of film with a stent configuration imprinted on each frame;

FIG. 6 is a side view illustration of the apparatus used to simultaneously rotate the coated tubular member, advance the film, and expose a portion of the outer surface of the tubular member to UV light;

FIG. 7 is a schematic representation of the processing step of immersing the coated tubular member to expose to UV light in a negative resist developer to yield an unrefined stent;

FIG. 8 is a schematic representation of the processing step of rinsing the excess negative resist developer from the unrefined stent;

FIG. 9 is a schematic representation of the processing step of chemically or electro-chemically treating the unrefined stent to a finished stent;

FIG. 10 is a perspective view of a stent resulting from the manufacturing process of the present invention;

FIG. 11 is a cross-sectional view of one configuration of the outer surface of a strut as seen along line 11—11 in FIG. 10 showing a trapezoidal protruding configuration that is directed radially from the longitudinal axis of the stent as a result of the present invention process;

FIG. 12 is a cross-sectional view of another configuration of the outer surface of a strut as seen along line 11—11 in FIG. 10 showing a triangular protruding configuration that is directed radially from the longitudinal axis of the stent as a result of the present invention process;

FIG. 13 is a cross-sectional view of another configuration of the outer surface of a strut as seen along line 11—11 in FIG. 10 showing a protrusion with a radius that is directed radially from the longitudinal axis of the stent as a result of the present invention process;

FIG. 16 is a cross-sectional view of the light source and the regulating platform;

FIG. 17 is a cross-sectional enlargement of the regulating platform of the apparatus; and FIG. 18 is a perspective view of the regulating platform.

DESCRIPTION OF THE PREFERRED EMBODIMENT

Figure 1:
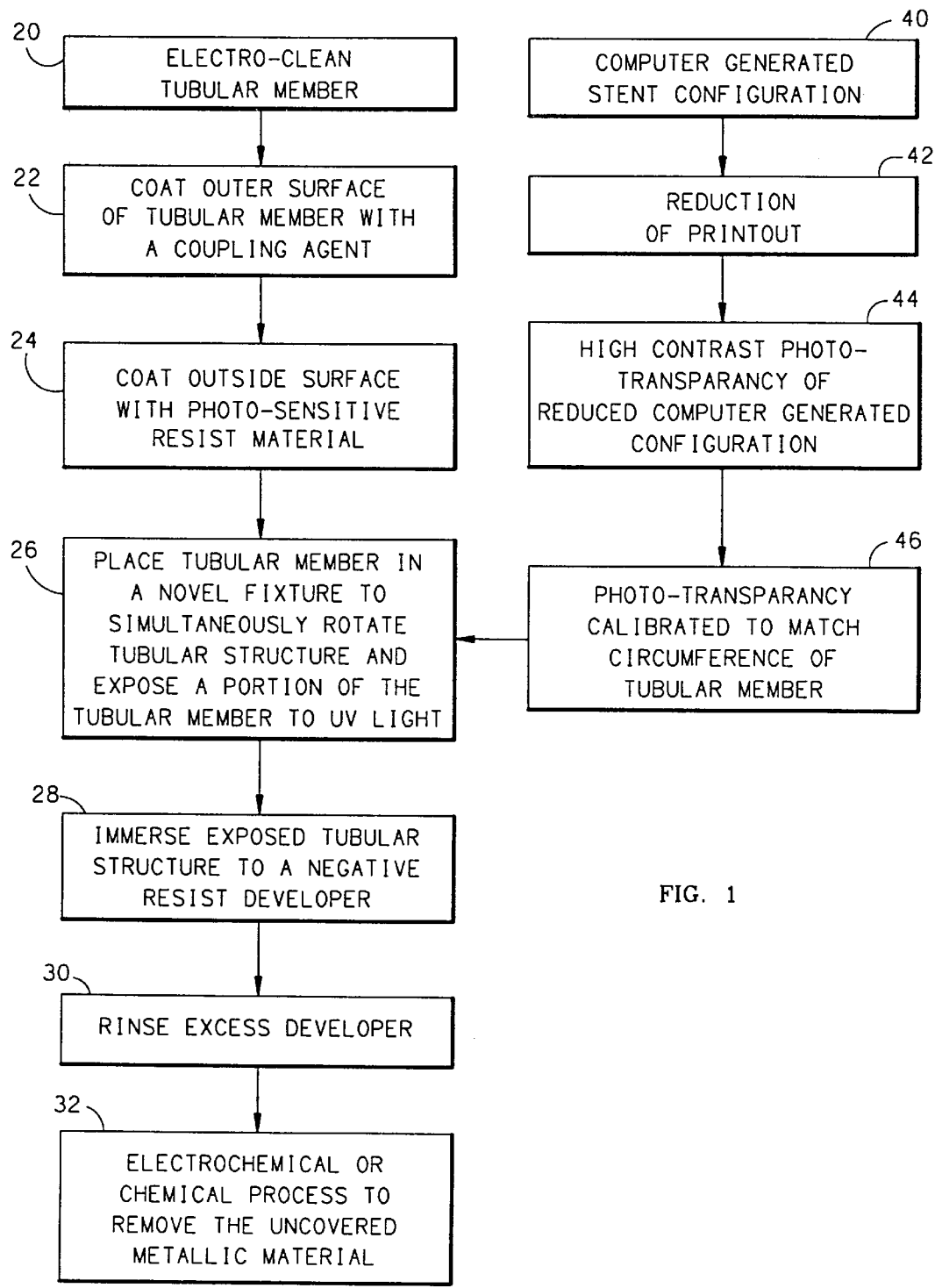
FIG. 1 is a flow chart illustration of the stent fabrication method of the present invention.

Reference is now made to FIG. 1, which illustrates the stent fabrication method of the present invention.

In the stent fabrication method of the present invention, a drawing representing a stent is designed on a computer that generates a printout with the desired stent pattern presented in a flat format 40. The pattern of step 40 can be printed on any size printout, but generally must be reduced to fit the requirements of photographic film 42 and the dimensions of the desired stent design. After the drawing of the stent pattern is reduced, it is transferred onto a high contrast transparent film 44. The final step requires that the phototransparent film be calibrated to match the circumference and dimensions of the tubular member employed in the fabrication process 46.

The tubular member can be any type of biocompatible materials, such as titanium, tantalum, stainless steel, platinum, gold alloy or gold/platinum alloy, a polymeric material or a material which is plated with a biocompatible material. The preferred candidate for stainless steel material for the tubular member is either the 316 or 321 stainless steel classes. The process of forming the tubular member is well known extrusion technology. It is preferable to have the tubular member relatively consistent in diameter, concentricity, thickness and seamless.

To process the particular tubular member, is it preferable to clean and remove contaminates 20. The tubular member can be further treated by exposing the cleaned tubular member to a temperature in the range of 100 to 200 degrees Celsius. Dependent on the tubular member's material and the photo-sensitive resist material employed, a coupling agent may be necessary to enhance the adhesion of the photo-sensitive resist to the outer surface of the tubular member. Therefore, after cleaning, the outside surface of the tubular member is optionally coated with a coupling agent 22. The processed tubular member is then coated with a photo-sensitive solution 24. Next, a novel apparatus is employed which exposes the resist coated tubular member to a specific pattern of UV light 26. The exposed tubular member is then immersed into a negative resist developer 28, whereby unexposed resist is removed from the processed tubular member.

FIG. 2 is a schematic view of the finished stent of the present invention in its intended operational environment. A stent resulting from the present invention can be used to treat atherosclerotic disease, prevent vessel recoil, overlie an aortic dissecting aneurysm, tack dissections to the vessel wall, and eliminate the risk of occlusion caused by flaps in both coronary native vessels and by-pass grafts. Stents can also be used to reinforce collapsing structures in the respiratory, biliary, urological, and other tracts.

For steps 20, 22 and 24, FIG. 3 demonstrates a simple means for exposing tubular member 64 to a cleaning solution 60, coupling agent 61, or the photo-sensitive resist 63 within a container 62. For example, Industroclean solvent detergent made by Amway Corporation is an example of suitable commercially available cleaning solution. A number of organo-silane coupling agents may be employed with the current invention process. Some examples of commercially available organo-silane coupling agents are vinyltriethoxysilane or methyltriethoxysilane made by Union Carbide and Z-6040 (containing glycidoxypropyltrimethoxysilane) or Z-6020 (containing aminoethylaminopropyltrimethoxysilane) made by Dow Corning. Probimide made by Olin Industries is an example of suitable commercially available photo-sensitive resist. When exposing the tubular member 64 with some commercially available photo-sensitive resists 63, the thickness of the resist polymer layer is dependent upon the amount of exposure time and possibly, the method of exposure or other variables. One method that can be employed to control the thickness of the photo-sensitive resists is to uniformly draw the tubular member(s) 64 through a solution of photo-resist for a specified period of time to obtain the desired coating layer. Furthermore, it may be desirable to protect the internal lumen of the tubular member from the photo-sensitive resist polymer during the exposure process.

It should be obvious to the one skilled in the art that standard methods of subjecting one or more tubular members to a cleaning solution are commercially available and can be employed with the present invention. In addition, it would be obvious to those skilled in the art to expose the cleaned tubular member to a heat source, preferably in the temperature range of 100 to 200 degrees Celsius, to facilitate drying of the tubular member. Furthermore, it should be obvious to one skilled in the art that standard methods of coating one or more tubular members with a coupling agent or photo-sensitive resist are commercially available and can be employed with the present invention. Having said this, subjecting tubular members of different metallic compositions may require different commercially available photo-sensitive resists or, if necessary, coupling agents.

FIG. 4-A demonstrates a cross-section of the outer surface of tubular member 64 coated with a photo-sensitive resist 66. In this example, the adhesion properties between tubular member 64 and the resist 66 is robust enough to not require an intermediate coupling agent layer. For example, using class 316 or 321 stainless steel for the tubular member with Probimide made by Olin Industries is an example of a suitable photo-sensitive resist/tubular member combination that does not need a coupling agent. It should be recognized by the artisan that there are several classes of polymers that can be employed with the present invention to function as a protective coating.

FIG. 4-B shows a cross-section of the outer surface of tubular member 64 coated with a photo-sensitive resist 66. Sandwiched between the tubular member 64 and resist 66 is a coupling agent 68. In this example, the adhesion properties requires the use of a coupling agent to facilitate and strengthen the bond between the tubular member 64 and the resist 66. For example, using gold alloy or platinum metal for the tubular member with Probimide photo-sensitive resist is an example of a combination that may need an organo-silane coupling agent to strengthen the bond between the tubular member and the resist.

FIGS. 5A and 5B show a preferred stent configuration imprinted on a transparent photographic film. The drawing of the pattern is generated on a computer program, reduced and printed onto a transparent film. For example, a stress analysis program called ALGOR was used to develop the computer generated printouts. The printout is then sent to a film processing facility who reduces the printout and generates a precisely dimensioned negative. As discussed in more detail below, the dimensions of the negative must be calibrated to render a specific stent design. Because of regulations concerning patent drawings which prohibit large blackened areas, an explanation of the drawings used to represent the photographic film is necessary. In FIGS. 5A and 5B, the open (transparent) spaces which allow the UV light to pass through the film are represented as solid black lines and alternating loops. The white areas of the drawings 5A and 5B represent the exposed (black) areas of the film which will block the UV light from passing through the film and exposing the underlying areas to UV. An example of a suitable film that can be employed in the present invention is Kodak ALI-4 Accumax film made by Kodak Industries. The length 77 of stent imprint is directly equal (1 to 1) to the circumference of tubular member 64. The width 75 is equivalent to the working length of the processed stent. FIG. 5B shows the transparent photographic film 76 with multiple frames 70 of the preferred stent configuration.

FIG. 6 shows sections of the apparatus including the ultraviolet lamp 82 laid-out in a typical configuration with sealed bulb 81 and filament 80 in an assembly. A regulating platform 84 comprises a base 84 with a top plate 88. A specially configured slit 87 centers the ultraviolet light into a narrow beam which reaches and penetrates the specific pattern of transparent film 76. Selected portions of the coated tubular member are illuminated with ultra-violet light which causes the exposed photo-resist to react and change its properties (cure and harden) and result in those portions remaining after electro-chemical etching as the stent struts 118.

The platform also comprises a rotating member 86 engaged with tubular member 64. Rotating member 86 moves in conjunction with the film passing over the rotating tubular member.

For step 28, FIG. 7 demonstrates a simple means for exposing tubular member 92 to a negative resist developer 90, within a container 94. It should be recognized by the artisan that there are numerous commercially available solvents for selectively removing the unexposed photosensitive resist of polymeric protective coating. It should also be obvious to the artisan that standard methods of exposing one or more tubular members with a negative resist developer can be employed.

FIG. 8 is a representation of step 30 where a means 100 is used to remove unexposed photo-sensitive resist or protective polymeric coating and rinse excess negative resist developer or other selective solvents from the partially exposed tubular member 92 using an appropriate solvent 102. In the preferred embodiment, QZ3501 made by Olin Industries is an example of suitable commercially available solvent to rinse the excess negative resist developer. At this time, the entire tubular member is incubated for a specified period of time, allowing the remaining photo-sensitive resist polymer to fully cure (harden) and attach to the surface of the processed tubular member. The tubular member can be incubated at room temperature or can be exposed to a heat source in the range of 100 to 400 degrees Celsius.

FIG. 9 is a representation of step 32 where an electro-chemical means is employed to remove the unexposed metallic material from the exposed tubular member 92. Shown in FIG. 9 is electro-chemical solution 110 contained within a member 116. In the preferred embodiment, a combination of phosphoric acid and sulfuric acids are employed to the etch unexposed metallic material. Hydrite 4000 made by Hydrite Industries is an example of suitable commercially available electro-chemical etching solution that contains the phosphoric and sulfuric acids. When employing a tubular member composed of stainless steel class 304, the preferred electro-chemical etching solution comprises a solution of ferric chloride. If the tubular member is composed of a gold alloy or platinum, other electro-chemical etching solutions, such as potassium cyanide, aqua regia (hydrochloride and nitric acids), or sodium hypochlorite may be required. To energize the etchant solutions, a negative charge is supplied through cathode 112 (which is immersed in the etchant solution) to the positively charged electrode 114 with is engaged to final tubular member 119 (of which both are immersed in the etchant solutions). Materials commonly employed as cathodes are platinum or gold. It should be obvious to one skilled in the art that standard methods of treating one or more tubular members with a electro-chemical means can be employed.

FIG. 10 is a representation of the preferred stent design 72 that results from the present invention method. The portions of the photoresist that were exposed to UV illumination and changed physical properties (cured and hardened) are retained during the electro-chemical process and remain intact as the struts or loops 118 of stent 72. The portions of the photoresist that were not exposed to UV illumination are removed during the electro-chemical process and result in open spaces 120. The structure resulting from a pattern of struts 118 and open spaces 120 comprises the desired stent configuration.

The present invention results in the preferred stent design 72 having specifically configured struts 118. FIGS. 11, 12, and 13 illustrate, in cross-section, three exemplary stent strut designs. As demonstrated in FIG. 11, the preferred stent design has the outer portion of the struts protruding in a trapezoidal configuration 134 which is directed radially from the longitudinal axis of the stent. The pattern of the preferred stent employs cross-section FIG. 11 and has a series of loops (U-shaped) 118 and a single backbone running along the length of the stent, thereby forming the basic scaffold of the stent design.

The pattern of FIGS. 10 and 11 can be formed of any size; a preferable size is between 0.035 thousandths to 0.100 thousandths in diameter when formed (crimped). The expanded or deployed diameter ranges from 2.0 mm to 8.0 mm with a preferred range for coronary applications of 2.5 mm to 6.0 mm. The length of the stent is virtually constant from its initial formation length to its length when expanded and ranges from 2 mm to 50 mm, with a preferred length for coronary applications of 5 mm to 20 mm.

In an alternate embodiment, the pattern of stent 72 is similar to that of FIGS. 10 and 11 but differs in the outer portion of the strut comprising a triangular configuration 132 (FIG. 12) where the point of the triangle is directed radially from the longitudinal axis of the stent. In another alternate embodiment, the pattern of stent 72 is similar to that of FIGS. 10 and 11 but differs in the outer portion of the strut comprising an extended base with a radius 130 (FIG. 13) which is directly radially from the longitudinal axis of the stent.

Finally, the stent 72 can be polished to remove any excess material not properly removed by the process. The polishing can be performed mechanically, by rubbing a polishing stick having diamond dust on its outside inside the stent 72. Alternatively, an additional electro-polishing step can be utilized.

Figures 14, 15:
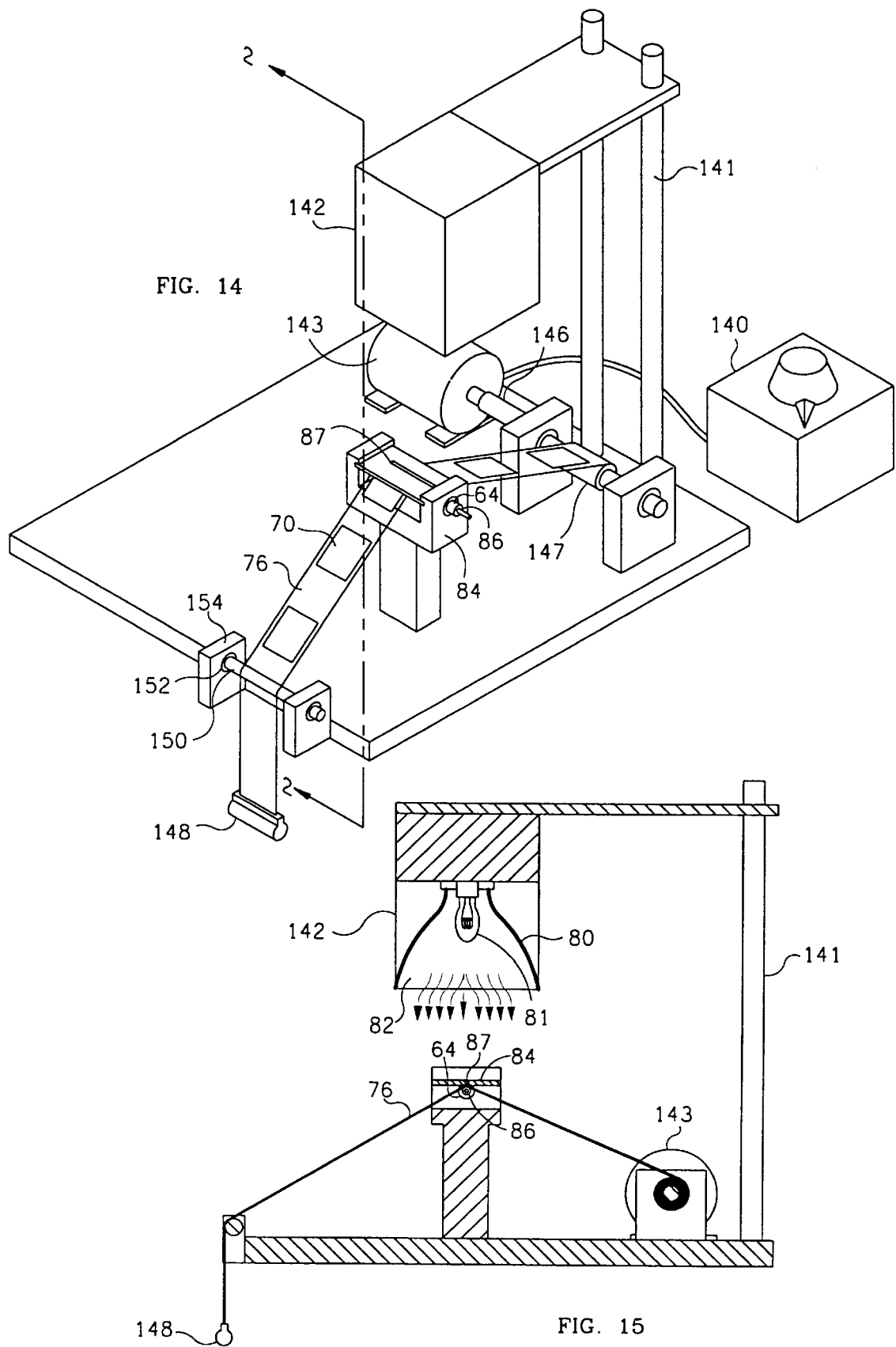
FIG. 14 is a perspective view of the apparatus used in the present invention stent fabrication process.
FIG. 15 is a cross-sectional view of the apparatus as seen along line 2—2 in FIG. 14 showing the perspective view of the apparatus.

FIG. 14 is a simplified perspective view of the apparatus used in the present invention stent fabrication process. Mounted on a stage is a supporting means 141 for locating the enclosure 142 containing UV light source 82 over the Y shaped regulating platform 84. The UV light source has a wavelength within the range of 360 to 440 nanometers with a preferred wavelength of 390 nanometers.

A series of repeating stent patterns or individual frames 70 are imprinted on a spool of film 147 which is engaged to rotating shaft 146. A motor 143 is engaged to and rotates the shaft 146 which speed is regulated by controller 140. Mounted also on the stage is regulating platform 84 which supports the coated tubular member 64 engaged to a rotatable shaft 86. The top of the regulating platform comprises a plate which is mounted within two horizontal inward facing slots cut into regulating platform 84. The top contains a specifically configured centering slit 87 positioned over the film 76 and coated tubular member 64. The function of the configured slit is to act as a slit lens and center the UV light obtained from the light source onto the narrow region of the film. In this simplified example of the apparatus, the film engages the tubular member 64 which is free to rotate on shaft 86. The movement of the photographic film over the tubular member 64 generates a rotational force which is in unison with the advancement of the film. An alternate method not shown would be to use a synchronized motor mechanism that would control both the advancement of the film and the corresponding rotation of the tubular member. Also not shown is a means to automatically remove the exposed tubular member 92 from the regulating platform and replacing with a coated tubular member 64. The automatic mechanism needs to correspond with the movement of the film to replace the tubular member between individual stent patterns (frames) 70.

Mounted on the side of the stage is another supporting means 154 containing a rotatable shaft 150. A weight is suspended from the end of the photographic film 148 and functions to provide tension on the photographic film to ensure adequate engagement with coated tubular member 64. A take-up reel or any number of tensioning mechanisms can suffice for the weight 148.

FIG. 15 is a cross-sectional view of the apparatus as seen along line 2—2 in FIG. 14 showing the perspective view of the apparatus. This cross-sectional view shows the relative position of UV light source 82 over regulating platform 84, slit 87 and tubular member 64. It can be seen from this figure that weight 148 provides tension to maintain the engagement of the photographic film to the tubular member.

FIG. 16 is a cross-sectional view of the light source and the regulating platform. This view demonstrates the orientation of the light source 82 facing in the general direction of the regulating platform 84. Diffuse UV light (shown by the arrows emanating from the light source) enter into specially configured slit 87. The figure also demonstrates one embodiment of the apparatus where the forward advancement of the photographic film 76 (shown by arrow) generates a rotational force (shown as clockwise) on the coated tubular member 64 which moves in unison with the film.

FIG. 17 is a cross-sectional enlargement of the regulating platform of the apparatus, specifically demonstrating the configuration of the focusing slit 87. Light enters beveled angles 90 which funnels the electromagnetic energy into a narrow channel 92 finally engaging photographic film 76. The pattern imprinted on the film blocks some of the light rays; while spaces in the pattern allow light to reach and react with the photo-sensitive resist on the coated tubular member 64. This process transfers the stent pattern from the relatively flat photographic film to the circular tubular member.

FIG. 18 is a side perspective view of the regulating platform. This figure shows a section of regulating platform 84, depicting one of the beveled angles 90 and one side of the narrow channel 92 of slit 87. Also demonstrated is that the width of beveled angle 90 and channel 92 is approximately equivalent to the width of the photographic film 76. Also shown is the photographic film 76 engaged with coated tubular member 64. Length 77 of frame 70 is designed and calibrated to equal the circumference of tubular member 64.

It is to be appreciated by persons skilled in the art that the present invention is not limited to what has been particularly shown and described hereinabove. Rather the scope of the present invention is defined only by the claims which follow:

We claim:

1. A stent fabrication method comprising the steps of:
    (a) Coating an outer surface of a metallic tubular member with a photo-sensitive resist resulting in a coated tubular member;
    (b) Placing said coated tubular member in an apparatus which simultaneously exposes a selected portion and shields other selected portions of said outer surface of said coated tubular member to a light source, yielding a partially exposed tubular member;
    (c) Immersing said partially exposed tubular member in a negative resist developer resulting in a treated tubular member;
    (d) Processing said treated tubular member by electro-chemical etching process to remove metal located in said selected portions of said tubular member shielded from said light source.

2. A stent fabrication method as recited in claim 1, further comprising the step of cleaning said tubular member prior to the step of coating said outer surface of said metallic tubular member with said photo-sensitive resist.

3. A stent fabrication method as recited in claim 1, further comprising the step of coating said outer surface of said tubular member with a coupling agent prior to the step of coating said outer surface of said metallic tubular member with said photo-sensitive resist.

4. A stent fabrication method as recited in claim 1, further comprising the step of incubating said treated tubular member in a temperature range, said temperature range being between 100 and 400 degrees Celsius, after the step of immersing said partially exposed tubular member to said negative resist developer.

5. A stent fabrication method as recited in claim 1, wherein said exposure of said light source to portions of said coated tubular member is regulated by a pattern imprinted on photographic film.

6. A stent fabrication method as recited in claim 2, further comprising the step of heating said tubular member in a temperature range, said temperature range being between 100 and 200 degrees Celsius, after the step of cleaning the tubular member.

7. A stent fabrication method as recited in claim 1, wherein said light source has a wavelength within the range of 360 to 440 nanometers.

8. A stent fabrication method as recited in claim 1, wherein said light source has a preferred wavelength optimized for the specific photoresist employed.

9. A stent fabrication method as recited in claim 3, wherein said coupling agent comprises a class of organo-silane compounds.

10. A stent fabrication method as recited claim 1, wherein a plurality of stents are made from a single piece of tubing.

11. A stent fabrication method as recited in claim 1, wherein said tubular member is made from a material selected from the group consisting of polymers, stainless steel, titanium, platinum, gold alloys, gold/platinum alloys and tantalum.

12. A stent fabrication method as recited in claim 1, wherein said electro-chemical etching process employs a solution of phosphoric acid and sulfuric acid.

13. A stent fabrication method as recited in claim 1, wherein said electro-chemical etching process employs a solution of ferric chloride.

14. A stent fabrication method as recited in claim 1, wherein said electro-chemical etching process employs a solution of potassium cyanide.

15. A stent fabrication method as recited in claim 1, wherein said electro-chemical etching process employs a solution sodium of hypochlorite.

16. A stent fabrication method as recited in claim 1, wherein said electro-chemical etching process employs a solution of hydrochloric acid and nitric acid.

17. A stent fabrication method comprising the steps of:
    (a) Coating an outer surface of a metallic tubular member with a photo-sensitive resist resulting in a coated tubular member;
    (b) Placing said coated tubular member in an apparatus which simultaneously rotates said coated tubular member in conjunction with an advancing photographic film which regulates the exposure of a selected portion and shields other selected portions of said outer surface of said coated tubular member to a light source, yielding a partially exposed tubular member;
    (c) Immersing said partially exposed tubular member in a negative resist developer resulting in a treated tubular member;
    (d) Processing the treated tubular member by chemical etching to remove a portion of uncovered metal.

18. A stent fabrication method as recited in claim 17, further comprising the step of cleaning said tubular member prior to the step of coating said outer surface of said metallic tubular member with said photo-sensitive resist.

19. A stent fabrication method as recited in claim 17, further comprising the step of coating said outer surface of said tubular member with a coupling agent prior to the step of coating said outer surface of said metallic tubular member with said photo-sensitive resist material.

20. A stent fabrication method as recited in claim 17, further comprising the step of incubating said treated tubular member in a temperature range, said temperature range being between 100 and 400 degrees Celsius, after the step of immersing said partially exposed tubular member to the negative resist developer.

21. A stent fabrication method as recited in claim 17, wherein said exposure of light source to portions of the stent is regulated by a stent configuration on transparent photographic film.

22. A stent fabrication method as recited in claim 18, further comprising the step of heating said tubular member in a temperature range, said temperature range being between 100 and 200 degrees Celsius, after the step of cleaning the tubular member.

23. A stent fabrication method as recited in claim 17, wherein said light source has a wavelength within the range of 360 to 440 nanometers.

24. A stent fabrication method as recited in claim 17, wherein said light source has a preferred wavelength optimized for the specific photoresist employed.

25. A stent fabrication method as recited in claim 19, wherein said coupling agent comprises a class of organo-silane compounds.

26. A stent fabrication method as recited claim 17, wherein a plurality of stents are made from a single piece of tubing.

27. A stent fabrication method as recited in claim 17, wherein said tubular member is made from a material selected from the group consisting of polymers, stainless steel, titanium, platinum, gold alloys, gold/platinum alloys and tantalum.

28. A stent fabrication method as recited in claim 17, wherein said electro-chemical etching process employs a solution of phosphoric acid and sulfuric acid.

29. A stent fabrication method as recited in claim 17, wherein said electro-chemical etching process employs a solution of ferric chloride.

30. A stent fabrication method as recited in claim 17, wherein said electro-chemical etching process employs a solution of potassium cyanide.

31. A stent fabrication method as recited in claim 17, wherein said electro-chemical etching process employs a solution of sodium hypochlorite.

32. A stent fabrication method as recited in claim 17, wherein said electro-chemical etching process employs a solution of hydrochloric acid and nitric acid.

33. A stent fabrication method comprising the steps of:
  (a) Coating an outer surface of a metallic tubular member with a protective polymeric coating resulting in a coated tubular member;
  (b) Placing said coated tubular member in an apparatus which simultaneously exposes a selected portion and shields other selected portions of said outer surface of said coated tubular member to a light source, resulting in some polymeric coating exposed and some polymeric coating unexposed, yielding a partially exposed tubular member;
  (c) Immersing said partially exposed tubular member in a solvent for selectively removing unexposed polymeric coating resulting in a treated tubular member;
  (d) Processing said treated tubular member by electro-chemical etching process to remove metal located in said selected portions of said tubular member shielded from said light source.

34. A stent fabrication method as recited in claim 33, wherein said protective polymeric coating comprises a class of photo-sensitive resists.

35. A stent fabrication method as recited in claim 33, wherein said solvent for selectively removing unexposed polymeric coating comprises a class of negative resist developers.

36. A stent fabrication method as recited in claim 33, further comprising the step of cleaning said tubular member prior to the step of coating said outer surface of said metallic tubular member with said protective polymeric coating.

37. A stent fabrication method as recited in claim 33, further comprising the step of coating said outer surface of said tubular member with a coupling agent prior to the step of coating said outer surface of said metallic tubular member with said protective polymeric coating.

38. A stent fabrication method as recited in claim 33, further comprising the step of incubating said treated tubular member in a temperature range, said temperature range being between 100 and 400 degrees Celsius, after the step of immersing said partially exposed tubular member to said solvent for selectively removing unexposed polymeric coating.

39. A stent fabrication method as recited in claim 33, wherein said exposure of said light source to portions of said coated tubular member is regulated by a pattern imprinted on photographic film.

40. A stent fabrication method as recited in claim 36, further comprising the step of heating said tubular member in a temperature range, said temperature range being between 100 and 200 degrees Celsius, after the step of cleaning the tubular member.

41. A stent fabrication method as recited in claim 33, wherein said light source has a wavelength within the range of 360 to 440 nanometers with a preferred wavelength of 390 nanometers.

42. A stent fabrication method as recited in claim 33, wherein said light source has a preferred wavelength optimized for the specific photoresist employed.

43. A stent fabrication method as recited in claim 37, wherein said coupling agent comprises a class of organo-silane compounds.

44. A stent fabrication method as recited claim 33, wherein a plurality of stents are made from a single piece of tubing.

45. A stent fabrication method as recited in claim 33, wherein said tubular member is made from a material selected from the group consisting of polymers, stainless steel, titanium, platinum, gold alloys, gold/platinum alloys and tantalum.

46. A stent fabrication method as recited in claim 33, wherein said electro-chemical etching process employs a solution of phosphoric acid and sulfuric acid.

47. A stent fabrication method as recited in claim 33, wherein said electro-chemical etching process employs a solution of ferric chloride.

48. A stent fabrication method as recited in claim 33, wherein said electro-chemical etching process employs a solution of potassium cyanide.

49. A stent fabrication method as recited in claim 33, wherein said electro-chemical etching process employs a solution of sodium hypochloride.

50. A stent fabrication method as recited in claim 33, wherein said electro-chemical etching process employs a solution of hydrochloric acid and nitric acid.

* * * * *

UNITED STATES PATENT AND TRADEMARK OFFICE
CERTIFICATE OF CORRECTION

PATENT NO. : 5,902,475
DATED : May 11, 1999
INVENTOR(S) : Thomas Trozera and Gary W. Gomringer It is certified that error appears in the above-identified patent and that said Letters Patent is hereby corrected as shown below:

```
ABSTRACT, line 15, insert the word "and" between "member, f)"
ABSTRACT, line 16, replace the word "a" with the word "an"
Column 2, line 27, replace the word "form" with the word "from"
Column 3, line 3, remove the comma between "patterns, of"
Column 3, line 12, insert a comma between "light thus"
Column 3, line 38, insert a comma between "process one"
Column 3, line 40, replace the word "appreciate" with the word "appreciated"
Column 4, line 63, insert a comma between "thickness and"
Column 4, line 64, replace the words "is it" with the words "it is"
Column 7, line 38, replace the word "with" with the word "which"
Column 7, line 43, replace the word "a" with the word "an"
Column 8, line 20, remove the comma between "mechanically, by"
Column 10, Claim 10, line 24, insert the word "in" between "recited claim"
```

Signed and Sealed this

Twenty-fourth Day of October, 2000

*Attest:*

Q. TODD DICKINSON

*Attesting Officer*  *Director of Patents and Trademarks*